United States Patent
Boyd et al.

(10) Patent No.: US 8,491,945 B2
(45) Date of Patent: Jul. 23, 2013

(54) **ORAL COMPOSITIONS CONTAINING OXIDIZED *CAMELLIA***

(75) Inventors: Thomas J. Boyd, Metuchen, NJ (US); Abdul Gaffar, Princeton, NJ (US); David Viscio, Prescott Valley, AZ (US)

(73) Assignee: Colgate-Palmolive Company, New York, NY (US)

( * ) Notice: Subject to any disclaimer, the term of this patent is extended or adjusted under 35 U.S.C. 154(b) by 14 days.

(21) Appl. No.: 13/354,645

(22) Filed: Jan. 20, 2012

(65) Prior Publication Data

US 2012/0114567 A1 May 10, 2012

Related U.S. Application Data

(62) Division of application No. 12/098,802, filed on Apr. 7, 2008, now Pat. No. 8,137,713, which is a division of application No. 11/256,776, filed on Oct. 24, 2005, now abandoned.

(60) Provisional application No. 60/639,169, filed on Dec. 23, 2004.

(51) Int. Cl.
*A61K 36/82* (2006.01)
*A61K 8/97* (2006.01)

(52) U.S. Cl.
USPC ............................................ 424/729; 424/58

(58) Field of Classification Search
None
See application file for complete search history.

(56) References Cited

U.S. PATENT DOCUMENTS

| | | | |
|---|---|---|---|
| 4,627,977 A | 12/1986 | Gaffar et al. | |
| 4,752,410 A | 6/1988 | Matsumura | |
| 4,894,220 A | 1/1990 | Nabi et al. | |
| 4,961,924 A | 10/1990 | Suhonen | |
| 5,080,887 A | 1/1992 | Gaffar et al. | |
| 5,202,112 A | 4/1993 | Prencipe et al. | |
| 5,292,526 A | 3/1994 | Gaffar et al. | |
| 5,409,692 A | 4/1995 | Nakahara et al. | |
| 5,538,715 A | 7/1996 | Gaffar et al. | |
| 5,611,939 A | 3/1997 | Hernandez-Mena et al. | |
| 5,681,548 A | 10/1997 | Esposito et al. | |
| 5,723,500 A | 3/1998 | Stringer et al. | |
| 5,776,435 A | 7/1998 | Gaffar et al. | |
| 5,912,274 A | 6/1999 | Stringer et al. | |
| 6,290,933 B1 | 9/2001 | Durga et al. | |
| 6,403,059 B1 | 6/2002 | Martin et al. | |
| 6,685,921 B2 | 2/2004 | Lawlor | |
| 2003/0206874 A1 | 11/2003 | Doyle et al. | |
| 2006/0127329 A1* | 6/2006 | Xu et al. | 424/57 |
| 2006/0134286 A1 | 6/2006 | Maeda | |
| 2006/0165622 A1* | 7/2006 | Hiramoto et al. | 424/65 |
| 2006/0188589 A1* | 8/2006 | Mezine et al. | 424/747 |
| 2007/0053849 A1* | 3/2007 | Doyle et al. | 424/50 |
| 2008/0003186 A1* | 1/2008 | Imai et al. | 424/49 |
| 2009/0087401 A1* | 4/2009 | Hiramoto et al. | 424/76.1 |

FOREIGN PATENT DOCUMENTS

| | | |
|---|---|---|
| CN | 1299818 | 6/2001 |
| EP | 0499332 | 10/1991 |
| EP | 919577 | 6/1999 |
| JP | 63036747 | 2/1988 |
| JP | 02025413 | 1/1990 |
| JP | 05186533 | 7/1993 |
| JP | 6263646 | 9/1994 |
| JP | 8034743 | 2/1996 |
| KR | 9005068 | 7/1990 |
| WO | WO 03/094878 | 11/2003 |

OTHER PUBLICATIONS

International Search Report issued in International Application No. PCT/US2005/046514 mailed on Jun. 21, 2006.
Matsumoto et al., "Molecular analysis of the inhibitory effects of oolong tea polyphenols on glucan-binding domain of recombinant glucosyltransferases from *Streptococcus mutans* MT8148," FEMS Microbiology Letters 228, 2003, pp. 73-80.
Nakahara et al. Appl. Environ. Microbiol. 1993. vol. 59, No. 4, pp. 968-973.
Ooshima et al. Caries Res. 1993. vol. 27, pp. 124-129.
Ooshima et al. Caries Res. 1998. vol. 32, pp. 75-80.
Ooshima et al., "Reduction of dental plaque deposition in humans by oolong tea extract," Biosciences Information Service, vol. 28, No. 3, 1994, pp. 146-149 (abstract only).
Wu et al. Nutrition. 2002. vol. 18, pp. 443-444.

\* cited by examiner

*Primary Examiner* — Chris R Tate
(74) *Attorney, Agent, or Firm* — Howard C. Lee

(57) ABSTRACT

Oral composition comprising a *Camellia* extract of semi-oxidized tissue from a member of the genus *Camellia* and an enhancing agent.

9 Claims, No Drawings

ORAL COMPOSITIONS CONTAINING OXIDIZED CAMELLIA

CROSS REFERENCE TO RELATED APPLICATION

This application is a divisional application of U.S. application Ser. No. 12/098,802, filed Apr. 7, 2008, which is a divisional application of U.S. application Ser. No. 11/256,776, filed Oct. 24, 2005, which claims priority to U.S. Provisional Patent Application No. 60/639,169 filed Dec. 23, 2004, the contents of each are incorporated herein by reference.

BACKGROUND OF THE INVENTION

Dental plaque is a biofilm that adheres to tooth and other oral surfaces, particularly at the gingival margin. Dental plaque is cohesive and highly resistant to removal from teeth and/or oral surfaces. Dental plaque comprises glucans, which are insoluble polysaccharides that provide plaque with its cohesive properties. The bacterial enzyme glucosyltransferase converts dietary sugar into glucans. Plaque mineralizes to form a hard deposit called calculus, which becomes a local irritant for the gums, causing gingivitis.

Current treatments for removing and preventing plaque build-up include brushing the teeth with an abrasive and/or antibacterial toothpaste, flossing, and various other treatments. The effectiveness of such treatments depends on a variety of factors including the amount of plaque present. While current techniques for removing and preventing plaque buildup on the teeth and oral tissues are suitable for their intended uses, they are subject to improvement.

BRIEF SUMMARY OF THE INVENTION

The present invention provides oral care compositions. Embodiments include oral compositions comprising: a *Camellia* extract of semi-oxidized tissue from a member of the genus *Camellia* and an enhancing agent.

The present invention still further provides for a method of using an oral composition for removing dental plaque and/or inhibiting deposition of dental plaque within an oral cavity. The oral composition comprises a *Camellia* extract of semi-oxidized tissue from a member of the genus *Camellia* and an enhancing agent.

The present invention still further provides for a method for removing dental plaque and/or inhibiting deposition of dental plaque within an oral cavity of a human or other animal subject comprising topically contacting teeth of said subject with an oral composition containing a *Camellia* extract of semi-oxidized tissue from a member of the genus *Camellia* and an enhancing agent.

The present invention also provides for an oral composition for at least one of inhibiting and removing dental plaque comprising a *Camellia* extract of semi-oxidized tissue from a member of the genus *Camellia*, an antibacterial agent, and an agent selected from the group consisting of synthetic polymeric polycarboxylate or a synthetic anionic polymeric phosphonate polymer having an average molecular weight of about from about 100 to about 1,000,000; orally acceptable surfactant, flavor oil, non-toxic alcohol, and solubilizing humectant; and mixtures thereof.

It has been discovered that compositions and methods of this invention afford advantages over oral care compositions known in the art, including one or more of enhancing the inhibition of bacterial film attachment to the teeth; and enhancing the removal of bacterial film from the teeth. Further uses, benefits and embodiments of the present invention are apparent from the description set forth herein.

DETAILED DESCRIPTION OF THE INVENTION

Oral compositions according to the present invention comprise an extract obtained from semi-oxidized tissue of a member of the genus *Camellia*. In various embodiments, the use of such an extract of semi-oxidized *Camellia* tissue and an enhancing agent in an oral composition for topical oral administration inhibits formation or accumulation of bacterial film (e.g. plaque) on the teeth and oral surfaces and/or assists removal of bacteria from the teeth and oral surfaces. The oral composition may optionally also include an antibacterial agent and a solubilizing agent. The oral compositions are suitable for use by human and other animal subjects.

The present invention additionally provides oral care compositions and methods for administration or application to, or use with, a human or other animal subject.

The present invention, in various embodiments, provides oral compositions for treating and/or inhibiting bacteria deposits (e.g., plaque) in the oral cavity, such as on the teeth and gums. The oral composition can be present in various different forms. For example, the oral composition can be at least one of a dentifrice, paste, gel, floss, tape, powder, mouth rinse, mouthwash, tooth hardener, oral film, anticalculus composition, antibacterial composition, film, slurry, and lozenge.

The present invention provides oral compositions comprising an extract derived from semi-oxidized plant tissues, preferably being or including leaves, of the genus *Camellia*, preferably *Camellia sinensis*. Any variety, form, or subspecies of *C. sinensis* may be used and these may be selected from any subspecific taxon thereof, preferred examples of which are: *C. sinensis* var. *assamica*, which includes, e.g., the former *C. assamica* and var. *kucha*; *C. sinensis* var. *cambodiensis*, which includes, e.g., the former subsp. *lasiocalyx* and var. *Shan*; *C. sinensis* var. *dehungensis*; *C. sinensis* var. *pubilimba*; and *C. sinensis* var. *sinensis*, which includes, e.g., the former vars. *bohea, macrophylla, parvifolia,* and *waldenae*. In a preferred embodiment, the *Camellia* extract will be made from semi-oxidized tissue(s) of *C. sinensis* var. *assamica, C. sinensis* var. *cambodiensis*, or *C. sinensis* var. *sinensis*; in a preferred embodiment, the extract will be made from semi-oxidized tissue(s) of *C. sinensis* var. *assamica* or *C. sinensis* var. *sinensis*; in a preferred embodiment, the extract will be made from semi-oxidized tissue(s) of *C. sinensis* var. *sinensis*.

The *Camellia* extract can be derived from a variety of different semi-oxidized tissues from members of the genus *Camellia*, with its associated subtaxa, such as one or more of semi-oxidized: leaves, leaf buds; flowers, flower buds; stems, twigs; stem, twig, and trunk bark; roots; root bark; and other aerial and reproductive parts. Preferably, semi-oxidized leaves, leaf buds, or both will be used. Preferably, semi-oxidized leaves will be used.

*Camellia* tissue(s) used for production of semi-oxidized tissues are generally processed according to the following exemplary procedure. Although the following traditional procedure is described with references to leaves, other tissues may be processed in a similar manner, and other non-traditional techniques may substitute or supplement in the steps described below; for example, vacuum may be employed to assist in the dehydration steps. As used herein, oxidized or a semi-oxidized "tea" includes any type of oxidized or semi-oxidized *Camellia* tissues.

As referred to herein, the term "oxidation" refers primarily to oxidation by at least one of the following processes: enzymatic oxidation; ambient air oxidation; and ambient photo-oxidation. In a preferred embodiment, oxidation is performed exclusively by one or more of the following processes: enzymatic oxidation; ambient air oxidation; and ambient photo-oxidation.

In addition, although the following description refers to a typical oolong tea preparation process, the same general steps (sun-wilting, shade-withering, rolling, "fermenting," and drying) can be employed to form any oxidized tea, including other semi-oxidized teas, e.g., pouchongs, as well as substantially fully oxidized teas, e.g., red teas, i.e. Western "black" teas. Fully and substantially fully oxidized teas that have been oxidized substantially more than 90%, e.g., above 95%, are generally not considered useful "semi-oxidized" teas herein. In the case of less-oxidized semi-oxidized teas, the time allowed for the below-described sun-wilting, shade-withering, rolling, and "fermentation" steps would be reduced; in the case of more-oxidized teas, the time allowed for these steps would be increased, e.g., red/black tea production commonly involves about 12-24 hours of shade-withering, and about 1-4 hours of "fermentation."

The leaves are harvested while green. In some cases in which a semi-oxidized, e.g., oolong, tea is to be made, only the more mature green leaves (which are larger, thicker, and waxier) are selected for processing. The freshly harvested tea leaves are wilted in the sun for about 30-60 minutes (or in some cases for up to about 3 hours). The sun-wilted leaves are then shade-withered. They are brought under shade (usually indoors) and placed on, e.g., bamboo, trays and gently agitated, e.g., by manually ruffling the leaves, one large handful at a time, or else by vigorously shaking the trays (about once per hour), resulting in "bruising" of the leaf edges and even air circulation, followed by continued drying under shade. Alternatively, the leaves may be "blown-dry" with a continuous stream of warm air to effect the shade-withering. The shade-withering process lasts about 5 to 8 hours, at the end of which the tea retains from about 55% to about 60% of its original water content.

The shade-withered leaves are next rolled, and then rested briefly in ambient air. First, the leaves are rolled, either mechanically or by hand, to begin compacting and shaping them (e.g., into twists), and optionally to begin cutting them. The rolling process disrupts leaf cell walls, causing release of oils and juices that coat and/or suffuse the leaf mass. These oils and juices can then be readily oxidized during the "fermentation" step. Preferably, the rolling will be performed in an environment in which the temperature is about 20 to 25° C. and the relative humidity is about 90-95%, so that the leaf mass does not become dried out. The rolled leaves are placed on trays to rest. The resting permits the leaves to cool and results in a small degree of drying. Each rest typically lasts about 15-20 minutes. The rolling-resting step may be repeated, e.g., for total of about three cycles.

The rolled leaves are then "fermented" (i.e. allowed to oxidize): they are placed on trays or in troughs and maintained, for up to about 1 hour, in an environment that is typically at a temperature of about 10-40° C., more typically at about 20-25° C. "Fermentation" is then halted. To accomplish this, the "fermented" leaves are heated by roasting, or alternatively by pan-firing, to quickly, e.g., in about 5-15 minutes or less, raise the temperature of the leaves to a level, e.g., between about 50 and 100° C., at which catabolic enzymes in the leaf are denatured. Such enzymes include polyphenol oxidases (EC 1.10.3.1) and others.

In an alternative process, the order of the above-described steps may be altered so that the fermentation step either follows or is combined with the shade-withering step, in which case rolling (one or more times) is followed by the final drying step, which is described below; in such an alternative process, the agitation of the leaves during shade-withering can be much more vigorous, resulting in bruising and crushing of the leaves, e.g., by hand.

The "fermented" rolled leaves are then dried to about 4% to about 8% of original water content. In this step, the leaves are fired in a mechanical dryer or a roasting machine, although pan-firing can alternatively be used therefor. They are then spread on trays to cool. The cooled leaves may be re-fired and re-cooled once or twice more in order to obtain the desired low moisture content. The resulting oolong tea may be extracted using any suitable known extraction technique to provide an extract useful in the present invention. For example, extraction techniques that can be used include any suitable aqueous extraction or organic solvent extraction. Preferred extraction techniques utilize water, methanol, water/methanol, dichloromethane and methanol:THF. Any other suitable extraction technique may be used, such as steam distillation and supercritical fluid extraction.

The *Camellia* tissue is oxidized at least 5%; preferably about 10% or more; preferably about 15% or more; preferably about 20% or more; preferably about 25% or more. Preferably the *Camellia* tissue is oxidized about 90% or less; preferably about 85% or less; preferably about 80% or less; preferably about 75% or less; preferably about 70% or less; preferably about 65% or less; preferably about 60% or less. In a preferred embodiment the *Camellia* is oxidized about 5% to about 90%; preferably about 10% to about 90%; preferably about 15% to about 85%; preferably about 20% to about 80%; preferably about 20% to about 60%.

Any type of semi-oxidized *Camellia* tissue(s) preferably including semi-oxidized leaves, i.e. that have been oxidized from about 5% to about 90%, preferably from about 5% to about 80%, during processing may be used as a starting material for preparation of a *Camellia* extract according to the present invention. Such extracts may be obtained from any of the traditional "semi-fermented" teas, including those that belong to the traditional classes of "oolong"-type teas and "pouchong"-type teas, as well as other classes of tea whose leaves have been processed to result in about 5% to about 90% oxidation, regardless of how they are traditionally classed, e.g., white teas (Bai-Cha), yellow teas (Huang-Cha), blue or blue-green teas (Qing-Cha), or red teas (Hong-Cha).

Preferred examples of semi-oxidized teas include traditional oolong and traditional pouchong teas. Traditional oolong teas, also called woolong or Wu-Lung teas, are oxidized about 10% to about 80% during processing. Traditional oolongs are generally sub-classified as "green" oolong teas, oxidized about 10% to about 25%, and "red" oolong teas, also known as "dark" oolong teas, which have been oxidized about 25% to about 80%. Traditional pouchong teas, also called paochung or Bao-Zhong, are teas that have been oxidized about 5% to about 20%, more typically about 8% to about 18%. In a preferred embodiment, an oolong tea will be used to prepare a tea extract according to the present invention; in a preferred embodiment, a red oolong tea will be used.

Modern classifications also grade semi-oxidized teas according to their degree of oxidation. In a typical gradation, teas are classified as those that have undergone light oxidation (about 5% to about 20%), medium oxidation (about 20% to about 60%), or heavy oxidation (about 60% to about 90%).

Illustrative examples of common, commercially available types of semi-oxidized teas that fall within these categories are:
- Light oxidation—jade oolongs, pouchongs;
- Medium oxidation—Tung-Ting oolongs, Huan Jin Gui oolongs, Se Chung oolongs, Shui Hsien/Shu Xian oolongs, Ti-Kuan Yin oolongs, Wu-Yi oolongs, and amber oolongs;
- Heavy oxidation—Bai Hao oolongs, LiuPao oolong, Mandarin oolong, Penfun/Ponfeng oolongs, and champagne oolongs.

Other examples of common, commercially available types of traditional oolong teas include: Alishan/Kaoshan oolongs, Anxi oolongs, DaHongPao oolongs, Dancong oolongs, Mao Xie oolongs, Qilan oolongs, Tianli oolongs, Zhongshan Baiye oolongs, and Poobong Darjeeling oolongs. Any such semi-oxidized teas may be used. In a preferred embodiment, a tea that has been oxidized about 20% to about 80% will be used to prepare a tea extract according to the present invention; preferably an oolong tea that has been oxidized from about 20% to about 80% will be used. In a preferred embodiment, a "medium oxidation" (about 20% to about 60% oxidation-level) tea will be used to prepare a tea extract according to the present invention; in a preferred embodiment, an oolong tea that has been oxidized from about 20% to about 60% will be used.

The *Camellia* extract can be present in the oral composition at various amounts. For example, the *Camellia* extract can be present at more than about 0.001% by weight, from about 0.001% to about 10% by weight, from about 0.01% to about 8% by weight, from about 0.1% to about 5% by weight, and from about 1% to about 2% by weight.

The oral compositions preferably additionally comprise an enhancing agent (EA). The EA can be a water soluble or swellable anionic polymer or co-polymer comprising delivery enhancing groups and retention enhancing groups. The delivery enhancing groups enhance delivery of components of the *Camellia* extract to teeth and oral tissue. The retention enhancing groups enhance retention by the teeth and oral tissue of components of the *Camellia* extract.

The enhancing agents of the present invention can include, for example, those that are characterized as having utility as denture adhesives or fixatives or dental cements. The enhancing agent can be a polymer or copolymer, which terms are entirely generic, thus including, for example, oligomers, homopolymers, copolymers of two or more monomers, ionomers, block copolymers, graft copolymers, cross-liked polymers and copolymers, and the like. The EA can be natural or synthetic, and water (saliva) soluble or swellable (hydratable, hydrogel forming) polymer or copolymer. The EA can be selected to have various sizes, such as an average molecular weight (MW) of: about 100 to about 1,000,000; about 1,000 to about 1,000,000; or about 2,000-2,500 to about 250,000-500,000.

The EA can be a synthetic anionic polymeric or linear anionic polymeric polycarboxylate having an average MW of about 100 to about 1,000,000, or about 1,000 to about 1,000,000, and can be present in the oral composition from about 0.0005% to about 5% by weight, from about 0.005% to about 4% by weight, or from about 0.05% to about 3% by weight. The EA can be an anionic copolymer of maleic acid or anhydride with another ethylenically unsaturated polymerizable monomer. Preferably, the EA can be a vinylmethylether/maleic anhydride copolymer (PVM/MA), such as any one or more of the forms of GANTREZ® (available from ISP of Wayne, N.J.).

The delivery enhancing groups of the EA can be any of those listed in U.S. Pat. Nos. 5,538,715 and 5,776,435, which are incorporated by reference. In various embodiments, the delivery-enhancing group(s) are preferably acidic such as sulfonic, phosphinic, or more preferably phosphonic or carboxylic, or a salt thereof, e.g. alkali metal or ammonium. The delivery enhancing groups of the EA can be various phosphonates. Such phosphonate-type EA's can have an average MW from about 100 to about 1,000,000 or about 1,000 to about 1,000,000. The EA can be a polyvinyl phosphonate and/or alkali metal polyvinyl phosphonate and/or ammonium polyvinyl phosphonate of MW about 1000 or more. The phosphonate-type EA can be present in the oral composition from about 0.0005% to about 4% by weight. The EA can be a poly(β-styrenephosphonate), poly(α-styrenephosphonate), copoly(α-,β-styrenephosphonate) or another copolymer of α- or β-styrenephosphonate with another polymerizable ethylenically unsaturated monomer, such as copoly(β-styrenephosphonate/vinylphosphonate). The phosphonate-type EA can have an average MW from about 2,000 to about 30,000.

The retention enhancing group(s) can be any organic retention-enhancing group, for example, those that have the formula —$(X)_n$—R wherein X is O, N, S, SO, $SO_2$, P, PO or Si or the like, R is hydrophobic alkyl, alkenyl, acyl, aryl, alkaryl, aralkyl, heterocyclic or their inert-substituted derivatives, and n is zero or one or more. The aforesaid "inert-substituted derivatives," are intended to include substituents on R which are generally non-hydrophilic and do not significantly interfere with the desired functions of the EA as enhancing the delivery of the mixture (anti-bacterial agent) to, and retention thereof on, oral surfaces such as halo, e.g., Cl, Br, I, and carbo and the like.

As employed herein, the delivery-enhancing group refers to one that attaches or substantively, adhesively, cohesively or otherwise bonds the EA, carrying components of the *Camellia* extract, and the optional anti-bacterial agent, to oral (e.g. tooth and gum) surfaces, thereby "delivering" the *Camellia* extract and the optional anti-bacterial agent to such surfaces. The organic retention-enhancing group, which is generally hydrophobic, attaches or otherwise bonds components of the *Camellia* extract and the optional anti-bacterial agent to the EA, thereby promoting retention of these directly to the EA and indirectly to the oral surface(s). In some instances, attachment of components of the *Camellia* extract and the anti-bacterial agent occurs through physical entrapment thereof by the EA, especially when the EA is a cross-linked polymer, the structure of which inherently provides increased sites for such entrapment. The presence of a higher molecular weight, more hydrophobic cross-linking moiety in the cross-linked polymer still further promotes the physical entrapment of the components of the *Camellia* extract and the optional anti-bacterial agent in or on the cross-linked EA polymer.

When the oral composition is made by initially dissolving a polyphosphate and the optional anti-bacterial agent in a humectant and surface active agent and incrementally adding the EA to the resulting composition, especially where the EA is a polymeric polycarboxylate, the solution becomes clear and may be characterized as a "microemulsion." As the amount of EA therein increases such that the complete oral composition contains at least about 2.2% by weight thereof, the solution becomes cloudy and may be characterized as a "macroemulsion." In such "macroemulsion" type compositions, the anti-plaque effect of the optional anti-bacterial agent appears to be optimized.

In some embodiments the oral composition also comprises one or more solubilizing agents to solubilize the *Camellia* extract. The solubilizing agent can be any solubilizing agent that is effective to solubilize the *Camellia* extract. For example, in various embodiments the solubilizing agent can be at least one of an orally acceptable surfactant, flavoring oil, alcohol, and solubilizing humectant (e.g. propylene glycol).

Examples of surfactants that can be used include anionic, nonionic, amphoteric, zwitterionic, and cationic synthetic detergents. Anionic surfactants include the water-soluble salts of alkyl sulfates having 8-20 carbon atoms in the alkyl radical (such as sodium alkyl sulfate), a monoalkyl phosphate compound having 6-18 carbon atoms, the water-soluble salts of sulfonated monoglycerides of fatty acids having from 8-20 carbon atoms (such as sodium lauryl sulfate (>82% pure) and sodium coconut monoglyceride sulfonates), an alkyl glycoside that is mono[alkyl($C_{12}$-$C_{22}$)]-[(Glyc)1-20], sarcosinates (such as sodium and potassium salts of lauroyl sarcosinate, myristoyl sarcosinate, palmitoyl sarcosinate, stearoyl sarcosinate and oleoyl sarcosinate), taurates, higher alkyl sulfoacetates (such as sodium lauryl sulfoacetate), isothionates (such as sodium lauroyl isothionate), sodium laureth carboxylate, sodium dodecyl benezesulfonate, and mixtures of the foregoing. Preferred are the sarcosinates since they inhibit acid formation in the mouth due to carbohydrate breakdown. Nonionic surfactants include poloxamers (sold under the tradename PLURONIC); polyoxyethylene sorbitan esters (sold under the tradename TWEEN); fatty alcohol ethoxylates; polyethylene oxide condensates of alkyl phenols; products derived from the condensation of ethylene oxide with fatty acids, fatty alcohols, fatty amides, or polyhydric alcohols; and polypropyleneoxide or ethylene oxide condensates of aliphatic alcohols; long-chain tertiary amine oxides; long-chain tertiary phospine oxides; long-chain dialkyl sulfoxides; and mixtures of such materials. Amphoteric surfactants include betaines (such as cocamidopropylbetaine), derivatives of aliphatic secondary and tertiary amines in which the aliphatic radical can be a straight or branched chain and wherein one of the aliphatic substituents contains about 8-18 carbon atoms and one contains an anionic water-solubilizing group (such as carboxylate, sulfonate, sulfate, phosphate or phosphonate), and mixtures of such materials. Zwitterionic surfactants include derivatives of aliphatic quaternary ammonium, phosphonium and sulfonium compounds in which the aliphatic radical can be a straight or branched chain and wherein one of the aliphatic substituents contains about 8-18 carbon atoms and one contains an anionic water-solubilizing group (such as carboxy, sulfonate, sulfate, phosphate or phosphonate). Cationic surfactants include aliphatic quaternary ammonium compounds having one long alkyl chain containing about 8-18 carbon atoms (such as lauryl trimethylammonium chloride, cetylpyridinium chloride, cetyltrimethylammonium bromide, diisobuytylphenoxyethyldimethylbenzylammonium chloride, coconut alkyltrimethylammonium nitrite, cetylpyridinium fluoride). Certain cationic surfactants can also act as antimicrobials.

The solubilizing agent(s) can be present in various amounts, such as an amount sufficient to dissolve the *Camellia* extract, to prevent precipitation thereof upon dilution with the saliva. The solubilizing agent(s) can also be present in an amount effective to increase the uptake of the anti-bacterial agent and components of the *Camellia* extract by dental tissue. The solubilizing agent(s) are preferably present at about 0.02% to about 50% by weight.

Any suitable flavoring or sweetening material may also be used as a solubilizing agent and to enhance the palatability of the oral composition. Examples of suitable flavoring constituents are flavoring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, xylitol, sodium cyclamate, sucralose, perillartine, AMP (aspartyl phenylalanine, methyl ester), saccharine and the like. Suitably, flavor and sweetening agents may each or together comprise from about 0.1% to 5% more of the preparation. Flavoring oil is believed to aid the dissolving of the anti-bacterial agent. A phenolic flavor mixture consisting essentially of eucalyptol, thymol, methyl salicylate, and menthol can also be used.

The flavor and/or sweetening material can be present in any suitable amount. In various embodiments, the flavor and/or sweetening material can be present in an amount sufficient to dissolve the *Camellia* extract and prevent precipitation thereof upon dilution with saliva. In various embodiments, the flavor material can be present from about 0.5% to about 50% by weight of a solubilizing material for the anti-bacterial agent and/or the *Camellia* extract and in an amount sufficient to dissolve the anti-bacterial agent and/or the semi-oxidized extract in saliva. In various embodiments, the flavor can be present from about 0.02% to about 2% phenolic flavor mix in an amount such that the ratio of substantially water insoluble noncationic antibacterial agent:phenolic flavor is from about 5:1 to about 1:100. In various other embodiments, the flavor and/or sweetening material can be present in an amount effective to increase uptake of the anti-bacterial compound and/or components of the *Camellia* extract by dental tissue.

The oral composition can also include humectant polyols and esters to assist in dissolving components of the *Camellia* extract to permit delivery to the teeth and oral tissues. Any suitable humectant polyols and esters can be used, such as any one or more of: propylene glycol, dipropylene glycol and hexylene glycol; cellosolves such as methyl cellosolve and ethyl cellosolve; vegetable oils and waxes containing at least about 12 carbon atoms in a straight chain, such as olive oil, castor oil and glyceryl tristearate; and esters such as, amyl acetate, ethyl acetate, and benzyl benzoate. Petrolatum may also be used, as well as glycerine, sorbitol, and/or xylitol. Propylene glycol is preferred. As used herein, "propylene glycol" includes 1,2-propylene glycol and 1,3-propylene glycol. Propylene glycol can be present in any suitable amount, such as an amount sufficient to dissolve the semi-oxidized extract and the optional anti-bacterial agent and prevent precipitation thereof upon dilution with saliva.

The oral composition optionally comprises an effective anti-plaque amount of one or more anti-bacterial agents. Any suitable anti-bacterial or anti-plaque agent can be used. Orally acceptable antimicrobial agent among those useful herein include halogenated diphenyl ethers, benzoic esters, halogenated carbanilides, 8-hydroxyquinoline and salts thereof; zinc and stannous ion sources such as zinc citrate, zinc sulphate, zinc glycinate, sodium zinc citrate and stannous pyrophosphate; copper (II) compounds such as copper (II) chloride, fluoride, sulfate and hydroxide; phthalic acid and salts thereof such as magnesium monopotassium phthalate; sanguinarine; quaternary ammonium compounds, such as alkylpyridinium chlorides (e.g., cetylpyridinium chloride (CPC), combinations of CPC with zinc and/or enzymes, tetradecylpyridinium chloride, and N-tetradecyl-4-ethylpyridinium chloride,); bisguanides, such as chlorhexidine digluconate, hexetidine, octenidine, and alexidine; halogenated bisphenolic compounds, such as 2,2'methylenebis-(4-chloro-6-bromophenol); benzalkonium chloride; salicylanilide, halogenated salicylanilides; domiphen bromide; iodine; sulfonamides; bisbiguanides; phenolic compounds such as phenol and its homologs, mono- and poly-alkyl and aralkyl halophenols, and bisphenolic compounds; piperidino derivatives such as delmopinol and octapinol; magnolia extract; grapeseed extract; thymol; eugenol; menthol; geraniol; carvacrol; citral; eucalyptol; catechol; 4-allylcatechol; resorcinol and its derivatives, such as hexyl resorcinol; methyl salicylate; antibiotics such as augmentin, amoxicillin, tetracycline, doxycycline, minocycline, metronidazole, neomycin, kanamycin and clindamycin; and mixtures thereof. A further illustrative list of useful antibacterial agents is provided in U.S. Pat. No. 5,776,435, U.S. Pat. No. 5,681,548, U.S. Pat. No. 5,912,274 and U.S. Pat. No. 5,723,500.

In various embodiments, the anti-bacterial agent is a halogenated diphenyl ether, preferably 2',4,4'-trichloro-2-hydroxy-diphenyl ether (Triclosan). Triclosan can be present in the oral composition in various amounts, such as from about 0.001% to about 5% by weight, from about 0.01% to about 5% by weight, or from about 0.25% to about 0.35% by weight.

In various embodiments, the antibacterial agent can be a substantially water insoluble non-cationic anti-bacterial agent as discussed in U.S. Pat. No. 5,292,526, titled "Antibacterial Antiplaque Anticalculus Oral Composition," which is hereby incorporated by reference. Such antibacterial agents may be present in various amounts, such as about 0.01 to about 5% by weight.

The oral composition can also include at least one anticalculus composition, such as one or more of the anti-calculus compositions recited in U.S. Pat. No. 5,292,526 titled "Antibacterial Anti-plaque Anticalculus Oral Composition," which is incorporated herein by reference. In various embodiments, the anti-calculus composition includes one or more polyphosphates. The anti-calculus composition can include at least one wholly or partially neutralized alkali metal or ammonium tripolyphosphate or hexametaphosphate salt present in the oral composition at an effective anti-calculus amount. The anti-calculus composition can also include at least one water soluble, linear, molecularly dehydrated polyphosphate salt effective in an anticalculus amount. The anti-calculus composition can also include a mixture of potassium and sodium salts at least one of which is present in an effective anti-calculus amount as a polyphosphate anti-calculus agent. The anti-calculus composition can also contain an effective anticalculus amount of linear molecularly dehydrated polyphosphate salt anti-calculus agent present in a mixture of sodium and potassium salts. The ratio of potassium to sodium in the composition can be in the range of up to less than about 3:1. The polyphosphate can be present in the oral composition in various amounts, such as an amount wherein the weight ratio of polyphosphate ion to anti-bacterial agent ranges from in excess of from about 0.72:1 to less than about 4:1, or wherein the weight ratio of the anti-bacterial enhancing agent to the polyphosphate ion ranges from about 1:6 to about 2.7:1, or wherein the weight ratio of the anti-bacterial enhancing agent to the polyphosphate ranges from about 1:6 to about 2.7:1. Other useful anticalculus agents include polycarboxylate polymers and polyvinyl methyl ether/maleic anhydride (PVME/MA) copolymers, such as GANTREZ®.

In order to optimize the anticalculus effectiveness of the oral composition, inhibitors against enzymatic hydrolysis of the polyphosphate are desirably present. Such agents are an amount of a fluoride ion source sufficient to supply from about 25 ppm to about 5,000 ppm or from about 25 ppm to about 2,000 ppm of fluoride ions at about 0.001% to about 5% by weight, and about 0% to about 3% of a synthetic anionic polymeric polycarboxylate having a molecular weight of about 1,000 to about 1,000,000, preferably about 30,000 to about 500,000.

The oral compositions comprise an orally acceptable vehicle. Any suitable orally acceptable vehicle can be used, such as those described in U.S. Pat. No. 4,894,220 titled "Antibacterial Anti-Plaque Oral Composition," which is incorporated by reference herein. For example, the vehicle can include a water-phase with humectant. In the present invention, the water and humectant liquid phase can comprise at least about 10% by weight of the oral composition. Moreover, preferably the humectant comprises propylene glycol (and a substantially water-insoluble noncationic antibacterial agent). The remainder of the humectant is preferably glycerine and/or sorbitol and/or xylitol. Water is present typically in an amount of at least about 3% by weight; and glycerine and/or sorbitol and/or xylitol typically total from about 6.5% to about 75% by weight of the oral preparation, more typically from about 10% to about 75%, and, together with the solubilizing humectant, the essential humectant components typically amount to from about 7% to about 80% by weight of the oral preparation. Reference hereto to sorbitol refers to the material typically as available commercially in about 70% aqueous solutions. Where the composition contains a substantially water insoluble noncationic anti-bacterial agent, the composition will preferably be free of at least significant amounts of polyethylene glycol, particularly of average molecular weight of about 600 or more, since polyethylene glycol can inhibit the antibacterial activity of a noncationic antibacterial agent, even when another component, such as, propylene glycol is present to effect its solubilization.

The vehicle can also be a water-alcohol mixture. Generally, the weight ratio of water to alcohol is in the range of from about 1:1 to about 20:1, preferably from about 3:1 to about 10:1 and more preferably from about 4:1 to about 6:1. The total amount of water-alcohol mixture in, for example, a mouthwash is typically in the range of from about 70 to about 99.9% by weight. The alcohol is a non-toxic alcohol such as ethanol or isopropanol. A humectant, such as glycerine, sorbitol, or xylitol may be present in an amount of from about 10% to about 30% by weight. The oral composition may contain water at from about 5% to about 30% by weight. Liquid dentifrices typically contain about 50% to about 85% of water, may contain from about 0.5% to about 20% by weight of non-toxic alcohol and may also contain from about 10% to about 40% by weight of humectant, such as glycerine, sorbitol, and/or xylitol. Sorbitol refers to the material typically available commercially in about 70% aqueous solutions. Ethanol is the preferred non-toxic alcohol. The alcohol assists in dissolving the water-insoluble non-cationic antibacterial agent.

The oral composition can also include a thickening agent. Any suitable thickening agent can be used. For example, the thickening agent can comprise one or more of: carboxyvinyl polymers; carrageenans, also known as Irish moss, and more particularly iota-carrageenan; cellulosic polymers such as cellulose ethers, hydroxyethylcellulose, carboxymethylcellulose (carmellose) and salts thereof (e.g. carmellose sodium); natural gums such as karaya, xanthan, gum Arabic, and gum tragacanth; colloidal magnesium aluminum silicate, colloidal silica; and mixtures thereof. One or more thickening agents are optionally present in a total amount of about 0.001% to about 15%, for example from about 0.01% to about 10% or from about 0.1% to about 8% or from about 0.2% to about 5% by weight of the oral composition.

The compositions of the present invention optionally comprise an active material, which is operable for the prevention or treatment of a condition or disorder of hard or soft tissue of the oral cavity. Oral care actives, in addition to those set forth above, include whitening agents, anticaries agents, tartar control agents, periodontal actives, abrasives, breath freshening agents, malodour control agents, tooth desensitizers, salivary stimulants, and combinations thereof. It is understood that while general attributes of each of the above categories of actives may differ, there may some common attributes and any given material may serve multiple purposes within two or more of such categories of actives.

Actives useful herein are optionally present in the compositions of the present invention in safe and effective amounts. A "safe and effective" amount of an active is an amount that is sufficient to have the desired therapeutic or prophylactic effect in the human or lower animal subject to whom the active is administered, without undue adverse side effects (such as toxicity, irritation, or allergic response), commensurate with a reasonable benefit/risk ratio when used in the manner of this invention. The specific safe and effective amount of the active will vary with such factors as the particular condition being treated, the physical condition of the subject, the nature of concurrent therapy (if any), the specific active used, the specific dosage form, the carrier employed, and the desired dosage regimen.

Any suitable fluoride ion source can be present in the oral composition, such as those recited in U.S. Pat. No. 5,080,887 and titled "Antibacterial Anti-plaque, Anticalculus Oral Composition." Sources of fluoride ions, acid phosphatases, and pyrophosphatase enzyme inhibitors, are well known in the art as anti-caries agents. A fluoride ion source may be slightly soluble in water or may be fully water-soluble. They are characterized by their ability to release fluoride ions in water and by freedom from undesired reaction with other compounds of the oral preparation. Examples of such sources are inorganic metal and/or ammonium fluoride salts and compounds, such as, for example: sodium fluoride, potassium fluoride, ammonium fluoride, calcium fluoride; a copper fluoride, such as cuprous fluoride; zinc fluoride, barium fluoride; sodium silicafluoride, ammonium fluorosilicate, sodium fluorozirconate; and sodium monofluorophosphate, aluminum mono- and di-fluorophosphate, and fluorinated sodium calcium pyrophosphate. Amine fluorides, including olaflur (N'-octadecyltrimethylendiamine-N,N,N'-tris(2-ethanol)-dihydrofluoride) can also be used. Sodium fluoride, amine fluoride, stannous fluoride, sodium monofluorophosphate (MFP), and mixtures thereof are preferred.

The amount of fluoride-providing source is dependent to some extent upon the type of source, its solubility, and the type or oral preparation, but it will be present in a non-toxic amount, generally about 0.005 to about 3.0% in the preparation. In a dentifrice preparation, e.g. dental gel, toothpaste (including cream), toothpowder, or dental tablet, an amount of such source which releases up to about 5,000 ppm of $F^-$ ion by weight of the preparation is considered satisfactory. Any suitable minimum amount of such source may be used, but it is preferable to employ an amount sufficient to release about 300 to about 2,000 ppm, more preferably about 800 to about 1,500 ppm of fluoride ion.

The oral composition of the present invention can be made by any of the methods known in the art for combining ingredients to make oral care compositions. Examples of methods that can be used are set forth in: U.S. Pat. No. 6,403,059, titled "Methods Of Making Dentifrice Compositions and Products Thereof;" Clinical Pharmacology for Dental Professionals (Mosby-Year Book, Inc., 3rd ed. 1989); Mosby's Dental Hygiene: Concepts, Cases and Competencies, (Daniel, Susan J., Harfst, and Sherry A. eds., Elsevier Science Health Science Div. 2002); and Ernest W. Flick, Cosmetic and Toiletry Formulations, 2nd ed.).

The present invention provides for methods and processes of using the oral compositions of the present invention to treat and inhibit oral conditions, such as dental plaque deposits on the teeth and oral tissues, dental calculus, and oral inflammatory conditions. Further, the present invention provides for commercial packaging for the oral compositions to distribute and store the oral compositions.

The oral compositions can be applied to the subject in any suitable manner, as is known in the art. For example, the oral compositions can be applied to the subject's oral cavity using a suitable applicator or delivery device, such as a brush, dental strip, film, syringe, tape, gum, pill, or any other applicator or delivery device that is known in the art. The compositions can be used in prophylactic methods and processes to promote and maintain oral health, appearance, and breath freshness. The oral compositions can be repeatedly applied to the subject over a number of days according to a particular treatment schedule to treat and/or inhibit dental plaque deposits, dental calculus deposits, and oral inflammatory conditions. Instructions setting forth the treatment schedule can be provided with the commercial packaging.

The present invention is further illustrated through the following non-limiting example(s).

Example 1

A dentifrice composition of the present invention is made by combining the following ingredients:

TABLE 1

Dentifrice composition according to the present invention, which includes PVM/MA copolymer.

| INGREDIENT | WEIGHT % |
|---|---|
| Glycerin | 19.0 |
| Sorbitol | 21.0 |
| Propylene Glycol | 0.5 |
| Carboxymethylcellulose | 1.1 |
| Carageenan | 0.4 |
| Saccharin | 0.3 |
| Sodium fluoride | 0.243 |
| Titanium dioxide | 0.5 |
| PVM/MA | 2 |
| Sodium hydroxide (50%) | 1.2 |
| Silica | 21.5 |
| Sodium lauryl sulfate | 1.5 |
| Flavor | 1.0 |
| Oolong tea extract | 1.0 |
| Water to make 100% | |

The resulting dentifrice is a toothpaste that can be applied to the oral surfaces with a brush or other applicator.

The oral composition of Table 1, which includes PVM/MA copolymer, inhibits plaque from adhering to oral surfaces. It was surprising to learn that the PVM/MA copolymer boosts the effect of larger, more complex polyphenols present in the extract of semi-oxidized tea from genus *Camellia*. The polyphenols inhibit biofilm formation by interfering with the bacterial enzyme glucosyltransferase, which converts dietary sugar into insoluble polysaccharides called glucans. Glucans are included in the structure of dental plaque and make plaque biofilm cohesive and highly resistant to removal from teeth and other oral surfaces.

The examples and other embodiments described herein are exemplary and not intended to be limiting in describing the full scope of compositions and methods of this invention. Equivalent changes, modifications and variations of specific embodiments, materials, compositions and methods may be made within the scope of the present invention, with substantially similar results.

We claim:

1. An oral composition comprising:
   a *Camellia* extract, in an amount from about 1% to about 10% by weight of the composition, wherein said *Camellia* extract is obtained from a semi-oxidized tea from tissue which is oxidized about 60% or less;
   propylene glycol in an amount sufficient to dissolve the *Camellia* extract;
   an enhancing agent, wherein the enhancing agent is a vinylmethylether/maleic anhydride copolymer; and
   an orally acceptable vehicle.

2. A composition according to claim 1, wherein the *Camellia* extract is an Oolong tea extract.

3. A composition according to claim 1, wherein the semi-oxidized tea is oxidized about 20% to about 60%.

4. A composition according to claim 1, wherein the *Camellia* extract is present in the oral composition about 1% to about 5% by weight.

5. A composition according to claim 1 additionally comprising a solubilizing agent.

6. A composition according to claim 1, further comprising a fluoride ion source present in an amount sufficient to provide from about 25 to about 2,000 ppm of fluoride ion.

7. A composition according to claim 1, further comprising an antibacterial agent.

8. A composition according to claim 7, wherein the antibacterial agent is 2',4,4'-trichloro-2-hydroxy-diphenyl ether.

9. A composition according to claim 1, wherein the oral composition is at least one of a dentifrice, paste, or gel comprising a fluoride ion source present from about 0.001% to about 5%, a humectant present from about 10% to about 30%, water present from about 5% to about 30%, and water insoluble polishing agent present from about 10% to about 30%.

* * * * *